US006455609B1

(12) United States Patent
Rueggeberg et al.

(10) Patent No.: US 6,455,609 B1
(45) Date of Patent: Sep. 24, 2002

(54) FLUORIDE-RELEASING AMALGAM DENTAL RESTORATIVE MATERIAL

(75) Inventors: Fred Rueggeberg; Gary Whitford, both of Augusta; Don Mettenburg, Evans, all of GA (US)

(73) Assignee: MCG Research Institute Medical College of Georgia, Augusta, GA (US)

( * ) Notice: Subject to any disclaimer, the term of this patent is extended or adjusted under 35 U.S.C. 154(b) by 0 days.

(21) Appl. No.: 09/573,922

(22) Filed: May 18, 2000

(51) Int. Cl.$^7$ ................................................ A61K 6/05
(52) U.S. Cl. ..................................... 523/116; 433/228.1
(58) Field of Search .......................................... 523/116

(56) References Cited

U.S. PATENT DOCUMENTS

| | | |
|---|---|---|
| RE32,073 E | 1/1986 | Randklev |
| 4,738,722 A | 4/1988 | Ibsen et al. |
| RE33,100 E | 10/1989 | Ibsen et al. |
| 5,252,121 A | 10/1993 | Arnold |
| 5,273,574 A | 12/1993 | Arnold |
| 5,520,922 A * | 5/1996 | Gasser et al. ................ 523/116 |

FOREIGN PATENT DOCUMENTS

| | | |
|---|---|---|
| EP | 0 291 944 A1 | 11/1988 |
| JP | 56055305 A | 5/1981 |
| WO | WO 88/01859 | 3/1988 |

OTHER PUBLICATIONS

Bjorgtveit, et al., "Fluoride release from a fluoride–containing amalgam, a glass ionomer content and a silicate cement in artificial saliva," J. Oral Rehab., 8:237–241 (1981).

Fazzi, et al., "Fluoride release and physical properties of a fluoride–containing amalgam," J. Prosthet Dent., 38:526–531 (1977).

Skartveit, et al., "Fluoride release from a fluoride–containing amalgam in vivo," Scand J. Dent Res., 93:448–452 (1985).

Donly et al. "Demineralization inhibition at glass–ionomer cement and amalgam restoration margins in conjunction with additional fluoride regimens" Special Care in Dentistry 19(1) 24–8 (Jan.–Feb. 1999) (Abstract).

Tveit, et al. "Fluoride release from a fluoride–containing amalgam, a glass ionomer cement and a silicate cement in artificial saliva" Journal of Oral Rehabilitation 8(3) 237–41 (May 1981) (Abstract).

Donly "Enamel and dentin demineralization inhibition of fluoride–releasing materials" American Journal of Dentistry 7(5) 275–8 Ref. 36 (Oct. 1994) (Abstract).

* cited by examiner

Primary Examiner—Thurman K. Page
Assistant Examiner—Todd D Wapl
(74) Attorney, Agent, or Firm—Needle & Rosenberg, P.C.

(57) ABSTRACT

A fluoride-releasing dental amalgam composition for a tooth restoration comprising a dental amalgam alloy material and an fluoride-containing, the glass particulate powder component of a fluoride-leachable acid-etchable glass ionomer cement. The invention further provides a method for using the composition to prevent or reduce secondary caries in an existing tooth restoration, which is classified as a dental amalgam in nature.

4 Claims, No Drawings

FLUORIDE-RELEASING AMALGAM DENTAL RESTORATIVE MATERIAL

FIELD OF THE INVENTION

The present invention relates to a composition of a novel fluoride-releasing dental amalgam restorative material, which provides the capability to reduce the possibility of secondary decay approximate to a restoration as a result of fluoride release.

BACKGROUND OF THE INVENTION

Dental amalgam is one of the oldest of restorative material for direct replacement of missing tooth structure, and is still widely used today. Since its inception at the turn of the century, little significant change has been made to its composition, with the exception of the use of high copper materials during the last quarter century. It is one of the most technique-forgiving materials, and has met with long-term clinical success. One of the problems with this material is that it has no capacity to prevent formation of secondary decay in tooth structure surrounding the restoration. There are currently other classifications of dental restorative materials in use which offer such protection as a result of the slow release of fluoride from the material surface or bulk. Glass ionomer materials are one such type material, as well as various resin based products which have fluoride incorporated either into the polymer matrix, or in the inorganic filler particles. Compared to dental amalgam, however, glass ionomers are much more technique sensitive, and do not provide as good wear resistance in areas of high occlusal force.

The prior art of amalgam restoration placement involves preparing the remaining tooth structure to provide adequate resistance and retention form for the restorative material to prevent its loss via physical dislodgment during function. Such planning is required because dental amalgam is not chemically adherent to tooth structure. After preparation of the tooth tissues, it is typical that a lining material be placed over the cut tooth to provide for an early sealing effect. Such materials as copal varnish and more recently synthetic polymers have been used. Attempts at incorporating fluoride into this sealing agent have been performed to provide for fluoride release and provision of some degree of cariostatic action. However, some of these lining materials have been shown to dissolve over time, and are replaced by corrosion products of the dental amalgam, which then help to form a seal between prepared tooth tissue and the dental amalgam restoration. Also, materials used as restorative bases to provide thermal insulation to the tooth have been manufactured with fluoride as a potential leachable product. The concept of these materials is that if fluids and bacteria should migrate to this area, fluoride would be released and result in bacterial membrane instability, resulting in cell death.

If means to prevent recurrent decay from developing in a tooth fail, the entire restoration requires removal and replacement, resulting in enlargement of the preparation through the removal of additional tooth structure. It is not uncommon that this process would be repeated more than once, if an amalgam is placed at an early age. Thus, secondary decay around an amalgam restoration necessitates a possible series of replacements, each removing more tooth structure, resulting in a greatly weakened tooth. Indeed, it has been documented that approximately 53%–58% of the reasons for replacement of existing amalgam restoration in adult patients has been attributed to secondary caries (recurrent decay). See Mjör I A, Tandläkartdin, 71, 552–556, (1979) and Dahl J E., et al., Scand. J. Dent. Res., 86, 404–407, (1978). Replacement of existing amalgam restorations in deciduous teeth has also been highly correlated with secondary caries: 51% of the reason for amalgam replacement. See Mjör, I A., et al., NTF's Tidende, 96, 109–112, (1986).

Several studies have looked at the effect of fluoride releasing amalgams on the inhibition of caries. One study used calcium fluoride as the fluoride source in amalgam alloys and observed the effects of mercury, lactic acid, and fluoride concentration on fluoride release in the amalgam alloys. Fazzi, R., J. of Prosthetic Dent, 38, no. 5, 526–531 (1977). Another study compared the fluoride release from a fluoride containing amalgam, a silicate cement and a glass ionomer cement. This study concluded that the silicate cement and glass ionomer cement exhibited greater fluoride release than the fluoride containing amalgam. This study also indicated that less fluoride could be extracted from the glass ionomer cement powders. See Tveit, A. B. et al, J. of Oral Rehabilitation, 8, no. 3, 237–241, (1981). A later study by Skartveit, L., et al., Scandanavian Journal Dent. Research, 93, no. 5, 448452, (1985) reported that the release of fluoride ($SnF_2$) from an amalgam for a few weeks was probably sufficient to enhance remineralization.

U.S. Pat. No. Re. 32073 discloses a dental filling composition comprising a polymerizable resin binder and an inorganic glass filler which imparts opacity to X-rays.

U.S. Pat. No. 4,738,722 discloses a buffered glass ionomer cement which can be used as a base or liner under restorative materials, a luting cement and a core material for a cast restoration.

U.S. Pat. No. 5, 252,121 teaches tooth restoration comprising the application of a wet glass ionomer cement on a tooth lesion and placing an improved wet amalgam restorative on the wet glass ionomer cement and hardening.

U.S. Pat. No. 5,273,574 ('574) teaches a tooth restoration comprising a layer of glass ionomer cement bonded to the tooth and a layer of amalgam disposed on the layer of glass ionomer cement. U.S. '574 states that it is known in the art to add a silver alloy powder to glass ionomer cements, which are subsequently used as bases for amalgam restoratives. U.S. '574 also states that the corrosion that occurs as a result of the silver alloy additive might be overcome by the addition of a non-corrosive additive.

Currently, there are no commercial dental amalgam restorative materials which release fluoride. Development of such a material could greatly decrease the need for use of fluoride-releasing liners and bases, which may only provide temporary protection. If the component which releases fluoride is chemically bonded to the metallic portion of the amalgam matrix, the potential for fluoride release will not be lost. Should the outer surface become abraded or worn away, there will be additional bonded glass particles at the new surface to provide for fluoride release. Also, if the glass particle leaches fluoride in increased amounts upon acidic exposure, the released fluoride is correlated with environments which are most prone to result in tooth decalcification and overt decay. An additional benefit of the system is that the leached fluoride can be replenished in the glass particle as a result of the use of a fluoride containing dentrifice or the use of a topical fluoride treatment, as is commonly performed at periodic dental hygiene appointment.

None of the above-cited documents disclose compositions or methods, which achieve the above proposed system to solve the previously discussed problems in the art, such as those claimed herein.

SUMMARY OF THE INVENTION

The above-mentioned disadvantages with respect to the potential for secondary caries of dental amalgam restorative material are overcome by the use of the present invention. Specifically, the present invention consists of combining concepts of two major families of existing dental restorative materials, amalgams and glass ionomer.

In one embodiment the invention provides a fluoride releasing dental amalgam composition comprising a dental amalgam alloy material and the glass particulate powder component of a fluoride-containing acid etchable glass ionomer cement.

In another embodiment, the invention provides a method of preventing or reducing secondary caries around an existing tooth restoration comprising the step of placing the fluoride releasing dental amalgam composition in a prepared cavity area prone to tooth decalcification and/or overt decay.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of the invention and the examples included herein.

The present invention relates to a composition comprised of a novel dental amalgam restorative material that releases fluoride through the judicious incorporation of an acid-leachable glass component which has been preferably sintered with elemental silver. The silver contained in the glass becomes incorporated into the set amalgam matrix (gamma 1), thus chemically bonding the particle to the restoration surface. Upon exposure to an acid environment, the acid leachable glass particle at the restoration surface will elute small amounts of fluoride, which provides a cariostatic effect on surrounding tooth structure. The glass particles may be similar in concept and formulation to that currently used in a metal-reinforced ionomer dental restorative material. An additional advantage to this system is that the fluoride content of the glass particles can be recharged with the use of a fluoride-containing dentifrice, or with periodic applications of topical fluoride, such as performed at periodic dental hygiene visits. See Hatibovic-Kofman S., et al., *J. Dent. Res.*, 73, (abstract 260), 134 (1994) and Alvarez, A N, et al., *J. Dent. Res.*, 73 (abstract 259) 134 (1994).

It must be noted that, as used in the specification and the appended claims, the singular forms "a," "an" and "the" include plural referents unless the context clearly dictates otherwise.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

A weight percent of a component, unless specifically stated to the contrary, is based on the total weight of the formulation or composition in which the component is included.

In one embodiment the invention provides a fluoride releasing dental amalgam composition comprising a dental amalgam alloy material and the glass particulate powder component of a fluoride-containing acid etchable glass ionomer cement.

In another embodiment, the invention provides a method of preventing or reducing secondary caries around an existing tooth restoration comprising the step of placing the fluoride releasing dental amalgam composition in a prepared cavity area prone to tooth decalcification and/or overt decay.

As a restorative material, dental amalgam is packaged to have an alloy portion (termed gamma) and a mercury portion, Craig, R. G., *Restorative Dental Materials*, $10^{th}$ Edition, 209–243, Mosby, St. Louis, Mo. (1993). The alloy portion generally consists of the elements silver, copper, and in some cases small amounts of tin. The two elemental components are forcefully mixed in a trituration device, or amalgamator, to cause mercury to wet the alloy surface. Upon wetting, the alloy particle surface dissolves, resulting in elements selectively entering solution. Dissolved silver complexes with mercury forming the compound $Ag_2Hg_3$ (gamma 1), which hardens and holds the components together in a rigid mass. In some amalgams, the dissolved tin forms an undesired complex with mercury ($Sn_{7-8}$ Hg, termed gamma 2), which is much weaker and more prone to corrosion than the gamma 1 phase. Newer amalgams high in copper prevent the formation of this tin-mercury compound, favoring formation of a copper-tin compound ($Cu_6Sn_5$, the eta phase) and additional gamma 1.

Amalgam alloy as used herein, refers to an admixture of various alloyed metals, typically, tin, copper and/or silver with mercury. This admixture can result from the inclusion of two dissimilar shaped alloy particles, one which is spherical and the other which is irregular as a result of being processed by lathe-cutting. Only a few commercial alloy compositions include the incorporation of elements such as palladium and indium with the aforementioned elements.

A preferred dental amalgam is sold by Caulk Dentsply in Millford, Del., under the trade name DISPERSALLOY. DISPERSALLOY is a high-copper admixed material containing both lathe-cut and spherical alloy particles preproportioned in a capsule with appropriate amounts of elemental mercury. When placed in a triturator, a thin membrane is torn, allowing a mixture of mercury with the alloy powder, enhanced by the presence of a small plastic pestle. Any dental amalgam capable of bonding with elemental silver will function in this invention. The dental amalgam is present in the range of from about 0.1% to about 99.9% of the total composition, preferably from about 95% to about 99.9% of the total composition, more preferably from about 97% to about 99.9% of the total composition.

Glass ionomer cements, also known as glass ionomers, as used herein, refers to powders comprised of calcium aluminum silicate glass or aluminum fluoride type glass and a liquid comprising an aqueous solution of either polyacrylic acid, polymaleic acid or tartaric acid.

Glass ionomer restorative materials are typically powder-liquid systems consisting of a special acid etchable glass and a mixture of polyacrylic organic acids respectively. See Anusavice, K. J., *Science of Dental Materials*, $10^{th}$ Edition, 530–543, W.B. Saunders Co., Philadelphia, Pa. (1996). The glass is typically an acid-soluble calcium fluoroaluminosilicate. The generic composition of fluoroaluminosilicate glasses is: $SiO_2$ (41.9–35.2%), $Al_2O_3$ (28.6–20.1%), $AlF_3$ (1.6–2.4%), $CaF_2$ (15.1–20.1%), NaF (9.3–3.6%) and $AlPO_4$ (3.8–12.0%). Upon mixture of these two substances (acid etchable glass and polyacrylic organic acid), the organic acid attacks the outer glass particle, causing the leachable components to enter into solution. The released calcium ions link together the long polyacrylic acid chains through chelation bonding causing a setting reaction when sufficient lengths of cross-linked acids precipitate from solution. Later in the setting process, aluminum causes increased cross-linking and enhances restoration properties. In an attempt to increase some physical properties of the brittle restorative material, manufactures have added metals to the glass powder. In one method, the metal and glass are sintered, resulting in the incorporation of the element silver into the particle glass itself. In this invention, silver-sintered glass ionomer powder particles are preferably utilized. Such a combination of metal and glass ionomer particle has been termed a "CERMET." Non-sintered, i.e., non-metal, ionomer cement glass powders may also be utilized; however, enhanced particle retention is best achieved when the ionomer cement glass powder is coated with a metal that is capable of reacting with the amalgam during setting.

A preferred acid-etchable glass ionomer powder used in this invention is sold by ESPE Corporation of Seefeld, Germany under the brand name of KETAC-SILVER. The acid-etchable glass powder used in this invention is derived from the powder portion of the glass ionomer product. Preferably, the powder portion contains acid-etchable glass that has been sintered with elemental silver. However, any acid-etchable, fluoride-releasing glass component containing elemental silver, or some other inorganic component capable of reacting with and bonding to the setting amalgam matrix will work as well. The acid-etchable glass ionomer cement sintered with elemental silver is present in the range of from about 99.9 to about 0.1% of the total composition, preferably from about 0.5% to about 5% of the total composition, more preferably from about 1% to about 4% of the total composition.

In another embodiment, the invention provides that the dental composition of sintered fluoride-containing, fluoride-leachable acid-etchable glass ionomer cement and the dental amalgam alloy form a chemical bond to one another resulting in the retention of the particles of glass ionomer cement throughout the bulk of the restoration and on the surface of the restoration by other than purely mechanical means. The chemical bond sets the amalgam material or matrix. The set amalgam material or matrix retains the sintered, acid-etchable, fluoride-releasing glass particle for an increased period over dental compositions containing a similar glass particle that has not been metal-sintered.

In another embodiment, the invention provides that the dental composition is present on the outer surface and within or throughout the material bulk of the amalgam material. The presence of the ionomer on the outer surface enhances the release of fluoride when the glass is in an acidic environment.

The anticipated setting reaction of the combination of dental amalgam components with the CERMET powder relies on the fact that the glass contains elemental silver available at the particle surface. This metal has the capability of entering into reaction with mercury introduced through the amalgam reaction and forming a gamma 1 complex. Such a formation chemically bonds the filler particle to the amalgam matrix, permitting enhanced particle retention over that solely by mechanical means, as when a non-metal containing glass particle is used. The retained glass particle also reacts to acid environments by leaching fluoride, as it does when present in the glass ionomer product. Through the combination of these two technologies, it is possible to combine the capability of fluoride release with the properties of a dental amalgam, and create a fluoride-releasing, metal-based dental restorative material.

In another embodiment, the invention provides using the dental composition to prevent secondary caries around an existing restoration by releasing fluoride to areas which are prone to tooth decalcification and/or overt decay.

The fluoride-leachable acid-etchable glass ionomers have the ability to replenish its fluoride-releasing capacity when the outer surface of the glass ionomer has been previously depleted of fluoride following acid attack. The fluoride releasing capacity is correlated with environments which are most prone to tooth decalcification and overt decay. The depleted or leached fluoride is replenished in the glass ionomers either continuously, by the presence of additional bonded glass particles, or periodically with a fluoride-containing dentrifice or topical fluoride treatment.

In another embodiment, the invention provides a tooth bonded to the fluoride releasing dental amalgam composition.

The compositions of the present invention may further comprise one or more additives that are typically utilized in restorative compositions. These additives include, but are not limited to, a metal base, a metal salt, a metal oxide, a metal hydroxide, zinc phosphate, magnesium sulfate, zircon, an inorganic or organic filler, polymeric materials, a radiopaque agent, an antioxidant, a stabilizer, a coupling agent, a dye, a pigment, and other conventional dental amalgam additives.

EXAMPLES

The following examples are put forth so as to provide those of ordinary skill in the art with a complete disclosure and description of how the compositions claimed herein are made and evaluated, and are intended to be purely exemplary of the invention and are not intended to limit the scope of what the inventors regard as their invention.

Example 1

Compressive Strength

To establish that the presence of the glass powder did not have a detrimental effect on the amalgam physical properties, the 1-hour compressive strength of amalgam with various proportions was determined. To make different mixtures of these components, the amalgam capsule was removed and opened, and the alloy powder was weighed. Then one of the five treatments were performed:

1. No change in alloy content was made. The metals were replaced directly into the capsules (Control Treatment).

2. 1% of the alloy weight was removed, and replaced with an equivalent weight of the glass powder (1% Subtractive).

3. 5% of the alloy weight was removed, and replaced with an equivalent weight of the glass powder (5% Subtractive).

4. 1% of the alloy weight was determined and was supplanted with an equivalent weight of the glass powder (1% Additive).

5. 5% of the alloy weight was determined and was supplanted with an equivalent weight of the glass powder (5% Additive).

Of the above five treatments in example 1, treatments #2 and #4 fall within the scope of the invention.

The composition of the amalgam alloy used in example 1 is known to one of skill in the art and may comprise the following components in the various ranges set forth below:

40–70% Silver

26–30% Tin

2–3% Copper

0–2% Zinc

The composition of glass ionomer particle used in example 1 is also known to one of skill in the art and may comprise the following components in the various ranges set forth below:

| | |
|---|---|
| $SiO_2$ | 41.9–35.2% |
| $Al_2O_3$ | 28.6–20.1% |
| $AlF_3$ | 1.6–2.4% |
| $CaF_2$ | 15.7–20.1% |
| NaF | 9.3–3.6% |
| $AlPO_4$ | 3.8–12.0% |

The glass ionomer particle composition ranges recited above does not include the weight of the elemental silver that is sintered onto the glass ionomer particle.

The amalgam was then mixed according to the manufacturer's instructions in a triturator, and cylindrical specimens (4 mm diagonal by 7–8 mm in length) were made according to the American Dental Association's Specification test for 1-hour compressive strength. See Council on Dental Materials and Devices, *J. Am. Dent Assoc.*, 95, 614–617, (1977). The order of specimen fabrication and testing was completely randomized in order to reduce the effect of operator error on the test results. After 1 hour of setting time, the specimens were tested at a cross-head speed of 0.25 mm/min using a Universal testing machine (model TTB, Instron Corporation, Canton, Mass.). The stress at specimen failure was recorded, and is presented in Table 1.

TABLE 1

1-Hour Compressive Strength of Amalgam* Specimens

| Composition | Mean Strength (MPA) | Standard Deviation |
|---|---|---|
| 5% Additive | 64.5 | 40.3 |
| 1% Additive | 157.8 | 7.6 |
| Control | 167.1 | 21.4 |
| 1% Subtractive | 164.8 | 14.7 |
| 5% Subtractive | 85.8 | 51 |

*DISPERSALLOY was used as the dental amalgam.

Statistical analysis of the results were performed using a 1-way ANOVA followed by Dunnett's 2-tailed t-test using the treatment "control" as control. The level of statistical significance was established at a pre-set alpha of 0.05. The results indicated the presence of a significant difference among mean values. The post-hoc analysis indicated that the following groups were statistically equivalent: control, 1% additive and 1% subtractive. The strength of the 5% groups were severely compromised from the amount of glass powder incorporated into the dental amalgam alloy. Thus, it has been shown, using commercially available materials, that the glass powder can be successfully added into the dental amalgam without compromising strength values.

Fluoride Release

In order to show that fluoride would be released into an aqueous solution from the glass-impregnated dental amalgam, additional specimens in the "1% additive" and "1% subtractive" groups were made as described above. There were five specimens in each group. In addition, five "control" specimens, which did not have glass powder added, were also prepared.

Each specimen was placed individually in a test tube containing 10 ml of deionized water. The tubes were swirled continuously on a rotary shaker. After 24 hours, the specimens were removed and placed in tubes containing 10 mL of fresh water. This procedure was repeated two more times. Thus, fluoride release rates from each of the 15 specimens were determined for four sequential 24-hour periods.

The solutions were analyzed for fluoride content using ion-specific electrode following overnight diffusion using the hexamethyldisiloxane (HMDS)-facilitated diffusion method described in Whitford, G. M., *Some Characteristics of Fluoride Analysis With the Electrode*, $2^{nd}$ Edition, 24–29, S. Karger, New York (1996). Table 2 contains the fluoride release rates expressed as nanograms of fluoride over 24 hours and as mean±SD (n=5).

TABLE 2

Fluoride Release From Test Specimens

| | GROUPS | | |
|---|---|---|---|
| 24-hour Period | Control | 1% Additive | 1% Subtractive |
| $1^{st}$ | 24.3 ± 5.5 | 1499 ± 157 | 1508 ± 2.7 |
| 2nd | 13.1 ± 1.6 | 731 ± 47 | 774 ± 97 |
| 3rd | 11.8 ± 1.4 | 459 ± 39 | 497 ± 45 |
| 4th | 10.2 ± 0.3 | 447 ± 38 | 442 ± 42 |

The release rates from the 1% Additive and 1% Subtractive groups did not differ with statistical significance, but both were significantly higher than those from Control group. In fact, the amounts of fluoride analyzed in the Control solutions were near the limit of detection, so that it is possible that virtually no fluoride was released from the Control specimens. Thus, it is demonstrated, using commercially available materials, that the glass powder can successfully be added into the dental amalgam in an amount which has been shown not to compromise restoration strength, and which will also release measurable amounts of fluoride.

Example 2

Preparation of the Fluoride Releasing Acid-etchable Dental Amalgam from a Combination of Existing Commercial Product Components Step 1

An amount of 100% by weight of packaged DISPERSALLOY containing alloy powder particles and 100% of the contained elemental mercury were placed in a plastic capsule and triturated, wherein a thin membrane was torn allowing mixture of the elemental mercury with the alloy powder, which was further mixed with a pestle to form an alloy/mercury complex. The trituration period for the mercury component was in accordance with the manufacturer's packaging instructions.

Step 2

To 100% of the amalgam alloy mixture was added 1% by weight of the powder portion of an acid etchable glass ionomer powder sintered with elemental silver. The resultant admixture was excellent for a fluoride-releasing dental amalgam restorative material, as it did not show amalgam strength degradation while providing evidence of significant fluoride leaching.

The recommended use for the fluoride-releasing dental amalgam materials of the invention are as a dental restoration material.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A fluoride-releasing dental amalgam composition for a tooth restoration comprising mixture of a dental amalgam alloy material and a glass particulate powder component of a fluoride-containing, fluoride-leachable acid-etchable glass ionomer cement, wherein the amalgam alloy material comprises:

40–70% Silver
   26–30% Tin
   2–30% Copper
   0–2% Zinc and the glass particulate powder comprises:

41.9–35.2% $SiO_2$
   28.6–20.1% $Al_2O_3$
   1.6–2.4% $AlF_3$.
   15.7–20.1% $CaF_2$
   9.3–3.6% NaF
   3.8–12.0% $AlPO_4$.

2. The fluoride-releasing dental amalgam composition of claim 1, wherein the glass particulate powder component of the fluoride-containing, fluoride-leachable acid-etchable glass ionomer cement is sintered with elemental silver.

3. The fluoride-releasing dental amalgam composition of claim 2, wherein the sintered glass particulate powder component of the fluoride-containing, fluoride-leachable acid-etchable glass ionomer cement and the dental amalgam alloy material form a chemical bond to each other, resulting in the retention of the glass ionomer cement throughout the bulk of the restoration and on the surface of the restoration by other than purely mechanical means.

4. The fluoride-releasing dental amalgam composition of claim 1, wherein the glass particulate powder component of the fluoride-containing, fluoride-leachable acid-etchable glass ionomer cement is present on the outer surface and throughout the bulk of the restoration of the amalgam material.

* * * * *